US010458998B2

(12) United States Patent
Alfredsson et al.

(10) Patent No.: US 10,458,998 B2
(45) Date of Patent: Oct. 29, 2019

(54) DEVICE FOR PROCESSING SAMPLES (75) Inventors: Magnus Alfredsson, Weinfelden (CH);
Konstantin Lutze, Männedorf (CH);
Thomas Deutschmann, Wuppertal
(DE); Patrick Widler, Freienbach
(CH); Samuel Farner, Wernetshausen
(CH); Ulf Friederichs, Berg TG (CH);
Axel Bützer, Breakfast Point (AU);
Jürg Aeschbacher, Hombrechtikon
(CH); Bruno Walder, Riedikon (CH)

(73) Assignee: QIAGEN GMBH, Hilden (DE)

(*) Notice: Subject to any disclaimer, the term of this patent is extended or adjusted under 35 U.S.C. 154(b) by 1238 days.

(21) Appl. No.: 12/375,359

(22) PCT Filed: Jul. 27, 2007

(86) PCT No.: PCT/EP2007/006684
§ 371 (c)(1),
(2), (4) Date: Aug. 25, 2009

(87) PCT Pub. No.: WO2008/012104
PCT Pub. Date: Jan. 31, 2008

(65) Prior Publication Data
US 2009/0305392 A1 Dec. 10, 2009

(30) Foreign Application Priority Data
Jul. 28, 2006 (EP) .................... 06015812

(51) Int. Cl.
*G01N 35/00* (2006.01)
*G16H 10/40* (2018.01)

(52) U.S. Cl.
CPC . *G01N 35/00871* (2013.01); *G01N 35/00712* (2013.01); *G16H 10/40* (2018.01);
(Continued)

(58) Field of Classification Search
CPC .. G01N 35/871; G01N 35/712; G01N 35/663;
G01N 35/98; G01N 35/99;
(Continued)

(56) References Cited

U.S. PATENT DOCUMENTS 5,428,470 A * 6/1995 Labriola, II ..... G01N 35/00584
398/109
2002/0028489 A1* 3/2002 Ammann et al. ............ 435/91.2
(Continued)

FOREIGN PATENT DOCUMENTS

WO WO-8705536 A1 * 9/1987 ............. B03C 1/284
WO 00/60362 10/2000
WO 03/090897 11/2003

OTHER PUBLICATIONS

International Preliminary Report on Patentability in PCT/EP2007/006685; dated Feb. 3, 2009 (9 pages).
(Continued)

*Primary Examiner* — William H. Beisner
*Assistant Examiner* — Danielle B Henkel
(74) *Attorney, Agent, or Firm* — McBee Moore Woodward & Vanik IP, LLC (57) ABSTRACT Device for sample processing, particularly sample conditioning as well as for the preparation and/or optionally for implementing a sequential process for an analyte from a biological sample, said device comprising a module for receiving and/or outputting at least one sample vessel or process vessel, a module for transporting a process vessel, a module for sample conditioning and a module for initiating a sequential process for an analyte. The modules are divided into at least two units that each possesses a control system, and which are connected through a first data bus.

21 Claims, 7 Drawing Sheets (52) U.S. Cl.
CPC ............... *G01N 35/00663* (2013.01); *G01N 2035/00326* (2013.01)

(58) Field of Classification Search
CPC ......... G01N 35/1065; G01N 2035/326; G01N 2035/356; G01N 2035/524; G01N 2035/437; G01N 2035/455; G01N 2035/103; B01F 9/14; B01F 2009/74; B01L 2200/147; B01L 2300/1822; B01L 2300/1827; B03C 2201/26; G16H 10/40
USPC ................. 435/286.1, 287.1; 3/286.1, 287.1
See application file for complete search history.

(56) References Cited

U.S. PATENT DOCUMENTS

| | | | |
|---|---|---|---|
| 2004/0033610 A1* | 2/2004 | Lovell et al. | 436/43 |
| 2004/0101189 A1* | 5/2004 | Green et al. | 382/133 |
| 2004/0175258 A1 | 9/2004 | Haas | |
| 2004/0241828 A1 | 12/2004 | Huau | |
| 2005/0075757 A1* | 4/2005 | Haas et al. | 700/245 |
| 2005/0158701 A1* | 7/2005 | West | C12M 41/48 435/3 |
| 2005/0172405 A1* | 8/2005 | Menkedick | A61B 5/1115 5/618 |

OTHER PUBLICATIONS

International Search Report dated Feb. 11, 2008 for PCT/EP2007/006684.

\* cited by examiner

DEVICE FOR PROCESSING SAMPLES

CROSS REFERENCE TO RELATED APPLICATIONS

This application is a § 371 National Stage Application of PCT/EP2007/006684 filed Jul. 27, 2007 which claims priority to European Application 06015812.8 filed Jul. 28, 2006, and U.S. Application 60/384,195 filed Jul. 28, 2006.

BACKGROUND OF THE INVENTION

Field of the Invention

The present invention relates to a device for processing biological samples, for example for the subsequent analysis of a biomolecule, particularly a nucleic acid or a protein, in this sample. The device is suitable, for example, for application purposes in biochemistry, molecular genetics, microbiology, medical diagnostics or forensic medicine.

Description of Related Art

In many technical fields, such as, for example, chemistry, biology, medicine or environmental technology, one needs to analyse, to process or to cause biological materials (e.g. liquids) to react with each other. For this purpose, the liquids or materials are filtered, cooled, heated, broken down into their constituent parts, washed, pipetted, or treated by means of other processes. Frequently, one needs to carry out a lengthy and complex sequence of processing steps in order to prepare the biological material. Moreover, in many cases a large number of different materials must be processed according to the same sequence, or series of the same materials have to be processed in parallel.

In this respect, processes in the field of sample preparation for preparations and/or diagnostic or analytical investigations have become increasingly important, particularly those comprising the isolation of nucleic acids and/or proteins as a process step. This is particularly true for automated processes, because a large number of samples can be prepared in a short time in this way. Thus, the requirements for an efficient screening and/or analysis with a medium to high sample throughput are established. This is critically important, as a purely manual handling of very large sample numbers is difficult to manage in practice and is cost intensive.

A well-known method for the purification of biomolecules is based on the steps of releasing the cell constituents of a biological sample ("lysis"), selectively binding one or a plurality of specific constituents from the resulting lysate onto a solid support or carrier ("binding"), eliminating unwanted constituents from the solid support or carrier ("washing"), and the dissolution/liberation of the required constituent ("elution").

In order to permit an adsorption and desorption during the purification of the biomolecules, special adsorption materials were developed, which are made of e.g. silicon oxide-containing materials, such as silica gel and which are mostly in the form of particles or filter elements. The materials have a surface, onto which bind the biomolecules to be isolated or the unwanted components to be separated, in a specific or non-specific process. As an alternative to adsorption onto the matrix, other purification processes retain the biomolecules on filter elements simply due to the effect of size exclusion. If a liquid that contains a biomolecule, such as e.g. a nucleic acid, flows through the filter element, then biomolecules above a certain size, or some of them, remain in the filter element, while the remainder passes through the filter element. The separation power in this case depends inter a/ia on the size of the analyte and frequently, small analytes cannot be separated in this way.

An additional known process, for which the size of the analyte is of less importance, concerns the addition of preferably magnetic or magnetisable particles that have a nucleic acid- or protein-adsorbing substance on their surface, and the subsequent separation of the particles from the remainder of the sample by a magnetic separation process. The biomolecule that has to be separated and which is bound to this type of particle surface or filter surface is recovered by contacting the surface with a liquid eluant, e.g. nuclease-free water. In this way the desired biomolecule is desorbed or dissolved (eluted) from the adsorption matrix and collected in a vessel.

It is known that the abovementioned process steps can be carried out in a single automated device. The samples for analysis—such as for example blood or urine—are usually transferred, either by the device or prior to insertion in the device, into one or a plurality of process vessels that are then subjected to a defined series of procedures in the device. The device usually delivers a carrier with a plurality of wells or vessels, into which the purified samples are dispensed.

The document WO 9916781 describes a process for isolating an analyte from a biological sample. It includes the steps of lysing the sample in a reaction vessel, adding a solid adsorption matrix, incubating under conditions, in which the analyte binds to the adsorption matrix, removing unbound sample constituents from the reaction vessel, incubating under conditions, in which the analyte is eluted from the adsorption matrix, and separating the eluate from the adsorption matrix. In addition, a suitable device for isolating an analyte from a biological sample is described, comprising a sample preparation device, a holding device for reagents, a first holding device for reaction vessels for sample preparation, a second holding device for reaction vessels and a robotic tool device.

SUMMARY OF THE INVENTION

Although the essential design of automatic sample preparation devices is known, the prior art leaves great scope for improvements. Accordingly, the object of the present invention is to develop a sample preparation device with an increased efficiency and ease of maintenance as well as simplified operation and thus a lower frequency of operating errors. In addition, a high degree of flexibility and variability should be provided to the operator as well as the prerequisites for a continuous process chain that does not require any further intervention and additional supervision from the user, once started.

This object is achieved by a device according to claims 1 or 2, a unit according to claim 9 and a module according to claim 15. Further details, advantages and aspects of the present invention result from the dependent claims, the description and the attached drawings.

The inventive device for sample processing, particularly for sample conditioning and preparation and/or optionally for carrying out a sequential process, in particular an amplification reaction for one or a plurality of analytes from a biological sample as well as for optionally carrying out an analysis of one or a plurality of analytes from a biological sample typically includes at least one module for input and/or output of at least one sample vessel, at least one module for transporting one or a plurality of reaction vessels, at least one module for sample conditioning, which is preferably a lysis module and/or an extraction module that preferably carries out a magnetic separation, at least one module for preparing a sequential reaction, in particular an amplification reaction and/or an analytical method for one or a plurality of analytes, optionally at least one module for carrying out a sequential reaction, in particular an amplification reaction and/or an analytical method for one or a plurality of analytes, and optionally at least one module for carrying out a detection of one or a plurality of analytes. The modules are divided into at least two units, wherein the module for sample conditioning is arranged in a first unit and the module for preparing a sequential process, particularly an amplification reaction and/or an analytical method for one or a plurality of analytes, is arranged in a second unit.

A further aspect of the invention relates to a device for sample processing, particularly for sample conditioning and preparation and/or optionally for carrying out a sequential process, in particular an amplification reaction for one or a plurality of analytes from a sample as well as for optionally carrying out an analysis of one or a plurality of analytes from a sample, which includes at least one module for input and/or output of one or a plurality of sample vessels, at least one module for transporting one or a plurality of reaction vessels, at least one module for sample conditioning, which is preferably a lysis module and/or an extraction module that preferably carries out a magnetic separation, at least one module for preparing a sequential reaction, in particular an amplification reaction and/or an analytical method for one or a plurality of analytes, optionally at least one module for carrying out a sequential reaction, in particular an amplification reaction and/or an analytical method for one or a plurality of analytes, and optionally at least one module for carrying out an analysis of one or a plurality of analytes. The modules are divided into at least two units and each possess their own control system, wherein the at least two units are connected through a first data bus.

DETAILED DESCRIPTION OF A PREFERRED EMBODIMENT

The inventive device offers a series of advantages that mainly result from the structural division into units and modules. The device is freely configurable and can be flexibly configured both before and after ordering. In particular, different processing levels can be realised depending on the requirements of the user. Thus, depending on the configuration of the device, the following completely mapped process levels can be realised, for example: starting from a sample in any sample vessel up to the extraction of an analyte after lysis of the sample, alternatively up to the preparation of a sequential process, such as an amplification reaction, for example a polymerase chain reaction (PCR) or a protein assay by the addition of reagents, alternatively up to the conclusion of an analysis, i.e. up to the final analytical result (primary tube to result).

Sample conditioning is particularly understood to mean the processes that lead from the introduction of the sample up to the purified analytes. This includes, for example lysis processes, in particular chemical or enzymatic lysis processes, and extraction processes that preferably include the binding of one or a plurality of target components onto a matrix, optionally the washing of the matrix to remove unwanted components from the matrix, the separation of the matrix with the bound target components and the desorption/dissolution (elution) of the target compound from the matrix.

Particularly when the target compounds, such as nucleic acids and proteins are found in difficultly releasable biological samples, the sample conditioning can also include upstream mechanical disruption processes which, however, do not necessarily have to proceed in the same unit as the other cited processes for sample conditioning. In general, all processes from the prior art for preparing media and isolating and/or concentrating biological target components are possible as the sample conditioning processes.

The biological sample to be processed can be a frozen or a non-frozen biological sample, wherein all biological samples known to the person skilled in the art can be used as the biological sample. Preferred biological samples are selected from the group comprising biomolecules, for example natural, preferably isolated linear, branched or circular nucleic acids, such as RNA, especially mRNA, siRNA, miRNA, snRNA, tRNA, hnRNA or Ribozymes, DNA and the like, synthetic or modified nucleic acids, for example oligonucleotides, particularly for the primer, probes or standards used for PCR, nucleic acids or PNAs (peptide nucleic acids) marked with digoxigenin, biotin or fluorescent dyes, preferably isolated proteins or oligopeptides, synthetic or modified proteins or oligopeptides, for example antibodies with fluorescence markers or coupled with enzymes, hormones, growth factors, lipids, oligosaccharides, polysaccharides, proteoglucanes, bodily fluids such as blood, sperm, cerebrospinal liquids, saliva, sputum or urine, liquids that are obtained when processing blood, such as serum or plasma, leucocyte fractions or "buffy coat", saliva, faecal matter, smears, aspirates, scurf, hair, skin fragments, forensic samples, food or environmental samples that comprise free or bonded biomolecules, particularly free or bonded nucleic acids, metabolic products, whole organisms, preferably non-living organisms, tissues of metazoa, preferably of insects and mammals, especially from humans, for example in the form of tissue sections or organs, isolated cells, for example in the form of adhering or suspended cell cultures, organella, for example chloroplasts or mitochondria, vesicles, cell nuclei or chromosomes, plants, plant parts, plant issue or plant cells, bacteria, viruses, viroids, prions, yeasts and fungi.

A freshly prepared biological sample is preferably used as a non-frozen biological sample, for example a fresh tissue sample or freshly isolated blood cells from a living or dead organism, or in the case of a synthetic biomolecule as the biological sample, freshly synthesised nucleic acids or proteins. According to the invention, a "fresh" biological sample is preferably understood to mean a sample that was taken, or synthesised, in the case of a synthetic biomolecule, not more than 96 hours previously. However, the designation "fresh" biological sample also includes such samples that have been removed within the previously mentioned period, but which were pre-treated for stabilisation, for example with conventional fixatives, such as for example formalin, with dyes, such as eosin, with antibodies and the like. The preparation of fresh cell samples or tissue samples can result from all methods of preparation known to the person skilled in the art for this purpose, for example in the case of a tissue sample by means of a scalpel, for example during an autopsy, in the case of a blood cell sample by centrifugation of freshly removed blood and the like.

A biological sample is preferably employed as a frozen biological sample, which, after having been isolated according to the previously described technique, is cooled down to temperatures of 0° C. or less, preferably to temperatures of −20° C. or less and most preferably to temperatures of −70° C. or less, for example by contact with liquid nitrogen.

The sample can be loaded in any form from vessels known from the prior art into the present device. Normally, this is an open primary vessel. For blood samples this is normally in a closed tube. It is also possible to supply the device with a sample that has already been pre-treated. The pre-treatment can concern, for example a sample transfer from a closed primary vessel into a process vessel or another vessel with easy access to the sample. Moreover, a pre-treatment of the sample can also have occurred earlier, such as a mechanical cell disruption or an enzymatic and/or chemical lysis. In this case, preferably no further lysis step would be carried out in the device.

Concerning the analytes that are preferably isolated after the sample conditioning and subjected to a sequential process, they are preferably natural, modified or synthetic nucleic acids or natural, modified or synthetic proteins or oligopeptides. The nucleic acids include all nucleic acids known to the person skilled in the art, especially ribonucleic acids (RNA), for example mRNA, siRNA, miRNA, snRNA, t-RNA, hnRNA or ribozymes, or deoxyribonucleic acids (DNA). Fundamentally all types of polynucleotides are concerned that include a N-glycoside or C-glycoside of a purine base or pyrimidine base. The nucleic acid can be single, double or multistranded, linear, branched or circular. It can correspond to a molecule occurring in cells, such as for example genomic DNA or messenger RNA (mRNA), or be produced in vitro such as complementary DNA (cDNA), reverse strand RNA (aRNA), or synthetic nucleic acids. The nucleic acid can consist of a few subunits, at least two subunits, preferably eight or more units, such as for example oligonucleotides, several hundred units up to several thousand subunits, such as for example expression vectors, or significantly more subunits such as genomic DNA. Preferably, the nucleic acid comprises the coding information for a polypeptide in functional connexion with regulatory sequences, which enable the expression of the polypeptide in the cell, into which the nucleic acid is incorporated or is naturally present. In a preferred embodiment, the nucleic acid is therefore an expression vector. In another embodiment it is a pDNA (plasmid DNA), an siRNA, an siRNA duplication or an siRNA heteroduplication, wherein the term "siRNA" is understood to mean ribonucleic acids with a length of about 22 nucleotides, which are formed from the splitting of a double stranded RNA (dsRNA) by the enzyme "Dicer" and are built into the enzyme complex "RISC" (RNA-induced silencing complex).

Sequential analyses are preferably understood to mean processes for quantitative and/or qualitative analysis known from the prior art as well as amplification processes. The amplification processes include in particular the polymerase chain reaction (PCR) and the ligase chain reaction (LCR) as well as WGA (Whole Genome Amplification), wherein for example, anchored, asymmetric, error prone, in situ, inverse, long range, real time and reverse transcriptase may be cited for the PCR.

All the analytical methods that are known and appear suitable to the person skilled in the art can be employed, selected from the group comprising optical microscopy, electron microscopy, confocal laser scanning microscopy, laser micro-dissection, scanning electron microscopy, western blotting, southern blotting, enzyme linked immonosorbent assay (ELISA), immune precipitation, affinity chromatography, mutation analysis, polyacrylamide gel electrophoresis (PAGE), especially the two-dimensional PAGE, HPLC, RFLP analysis (Restriction Fragment Length Polymorphism-Analysis), SAGE analysis (Serial Analysis of Gene Expression), FPLC analysis (Fast Protein Liquid Chromatography), mass spectrometry, for example MALDI-TOFF mass spectrometry or SELDI mass spectrometry, microarray analysis, LiquiChip analysis, analysis of the activity of enzymes, HLA-Typing, sequencing, Rnase protection analysis or primer extension analysis.

In the scope of the invention, the sequential processes also include modification reactions, such as methylation.

According to a preferred embodiment, provision is made to stock the reagents in the device for a series of defined processes, such that when changing between processes for different types of sample, only the desired process has to be input at the operator interface thus increasing the user friendliness, reducing the necessary manpower requirements and thereby helping to reduce costs.

Upstream of the module for sample conditioning is preferably connected a further module for sample conditioning, which is not a lysis or extraction module. In general, the upstream module can concern any process known from the prior art for preparing the media. Preferably, the upstream module represents a module for carrying out physical cell disruption processes or for withdrawing the sample from closed primary sample vessels, and moreover is preferably provided in an additional unit. Physical cell disruption processes should be understood to mean especially non-mechanical processes that exploit osmotic pressure, increased temperature, freeze drying and/or mechanical processes e.g. using ultra-sound, mills or homogenisers.

An optional module for carrying out an amplification reaction is preferably provided in an additional unit. Advantageous amplification processes have already been mentioned above.

Preferably, the units are each in their own housings that are essentially structurally separate and particularly preferably are removably connected with each other. After connecting the individual units together, an observer advantageously has the impression that there is a single piece of equipment.

Preferably, at least one of the units has one or a plurality of areas for storing unused and/or used consumables, said consumables being optionally stored in closable containers. In a preferred embodiment, the areas for used and unused consumables are arranged separately.

Consumables are understood to mean all materials that are not permanent components of the device or of the individual units or modules, and which are usually disposed of immediately after use or when empty, e.g. in the case of containers. Examples of consumables include pipette tips and other disposables used e.g. for extraction (such as magnetic shielding screens), any reagents used (such as buffers, lysis reagents, wash solutions and/or adsorption materials), process vessels (preferably reaction vessels and other vessels required for the process, such as washing vessels, mixing vessels and/or elution vessels), storage tanks, storage bins (both for unused reagents and intermediate products from the treatment processes and also for used or unused disposables and waste products).

Preferably, at least one of the units possesses a pipette module for transferring a biological sample between two vessels, particularly a sample vessel and one or a plurality of process vessels.

Preferably, a plurality of process vessels is used in the course of a process inside a unit. The samples or the process mixture are repeatedly transferred from one process vessel into another, preferably by the pipetting module. Alternatively, the continuous use of a reaction vessel during the process in a unit is also possible. In this case the sample is only transferred from one initial sample vessel into a process vessel and at the end of the process again transferred into an initial sample vessel. Alternatively, instead of an initial sample vessel, a process vessel can also be directly transferred to a further unit or can serve as the initial sample vessel.

The reaction volume used can be significantly increased over those of the prior art or of commercially available equipment, thereby permitting a greater sensitivity of the device. For example, 50 µl to 10 ml, preferably 0.1 to 5 ml, particularly preferably 0.5 to 3 ml are transferred from the sample into a reaction vessel, in a quite particularly preferred embodiment 1 ml.

After the extraction, the amount of eluant used for elution can be chosen such that the desired absorption concentration in the eluate is obtained. The amount of eluant should of course be large enough to avoid too high a loss in yield from the carrier material used for the extraction.

It can be advantageous to add a normalisation module in the sample-conditioning module or downstream of it. Usually, this measures the concentration of the analyte in the eluate by means of photometry. Normalisation modules per se are known in the prior art. After analyte concentration has been measured, a defined concentration can then be prepared by dilution for carrying out selected sequential processes.

Advantageously, when a normalisation module is directly connected, UV-transparent process vessels are used to collect the eluate, or the eluate solution is transferred into this type of vessel.

Generally, this type of normalisation module can be integrated into one of the available units, e.g. as the end of the unit for sample conditioning or at the beginning of the preparation of a sequential process. For the dilution itself, the pipetting module of the unit, in which the normalisation module is placed, could be used, for example. If the normalisation module is in the sample-conditioning unit, then the dilution can also take place in the downstream unit for the preparation of a sequential process. The latter is particularly preferred, as the unit for the preparation of sequential processes has usually a pipetting module with a very high accuracy and in spite of the dilution very high concentrations are usually required.

It is also possible to place the normalisation module, optionally with a pipetting module, in a separate unit that should be situated between the unit for sample conditioning and the unit for preparing a sequential process.

In a preferred embodiment of the invention, at least one unit has a microprocessor. A first data bus, preferably according to the Ethernet standard, connects the units together, wherein various topologies are possible, preferably a star starting from one unit, a ring or the connection over a "switch". The modules within one unit are preferably connected over a second data bus, preferably over a CAN bus. The modules within one unit preferably have a single interface to the second data bus. In a preferred embodiment, at least one of the modules within a unit comprises a microprocessor, preferably a microcontroller. In a further preferred embodiment, at least one microcontroller works with a real-time operating system.

Preferably, one module for accepting sample vessels can be adapted by means of adapters to accept a plurality of different sample vessels that are preferably commercially available sample or reaction vessels, such as quite common test tubes of various sizes, multi-well sample plates (e.g. 96, 48, 16, 12 or 8 well plates), PCR tubes or blood sample tubes.

Besides the acceptance, at least one unit can deliver sample vessels in various starting formats to another unit or for further manual processing. Whereas sample conditioning units and/or units for the preparation or for carrying out sequential processes are known from the prior art, they are usually only compatible together with one combination due to the predetermined input and output formats of equipment that mostly vary according to the different suppliers, it is instantly possible to select different input and output formats from different suppliers. Consequently, units of the present device, especially the unit for sample conditioning and the unit for preparing sequential processes, can be combined with different downstream and/or upstream units from other manufacturers and nevertheless permit a continuous process run. For PCR reactions as the sequential process, in particular any PCR tubes and PCR capillaries used in conventional cyclers can serve as the input format.

The transfer of the conditioned and/or treated samples into the desired output format preferably even occurs on the unit, on which the sample conditioning, particularly the lysis and/or extraction, also takes place. It would also be possible to carry out the transfer to the unit for the preparation of the sequential process.

Preferably, at least one unit of the device is designed to be connected with an external computer, so that parameters of the device can be adjusted and called, preferably parameters for process operations, types of sample vessels and/or process vessels and parameters of the consumables as well as log files and status reports of the device etc.

Preferably, a module for sample conditioning works as the extraction module that works according to a magnetic separation process. Preferably, an assembly of sleeves is adapted for the mounting, which serves to spatially separate a sample in a reaction vessel and a magnet used for the magnetic separation, preferably a permanent magnet. The sleeves are preferably arranged in a matrix or a plurality of matrices to form a whole.

Alternatively, the extraction module can also work with other processes known from the prior art for the separation of the carrier material or for magnetic separation.

Preferably, at least one of the units comprises an operator interface. Preferably, this can be realised in the form of a touch screen and serves for the input of information by an operator. Status information, input requests and possible device error messages are shown simultaneously on the monitor. According to a further preferred embodiment, a remote maintenance module affords the implementation of remote maintenance and remote diagnosis, for example over the Internet, for example through a support service or a manufacturer.

A further aspect of the invention relates to a unit for sample processing, which comprises a module for the input and/or output of one or a plurality of sample vessels, and one or a plurality of identical or different additional modules, selected from a group comprising:

(a) a module for transporting one or a plurality of reaction vessels inside the unit, (b) a transfer module for transporting one or a plurality of reaction vessels between two units, wherein the transfer module possesses a telescopic arm and/or a conveyor belt and preferably works bidirectionally, (c) a module for sample conditioning, which is a lysis module and/or an extraction module that preferably implements a magnetic separation, (d) a module for preparing a sequential process, in particular an amplification reaction and/or an analytical process, which is preferably a pipetting module and/or a cooling module, (e) a module for amplifying and/or analysing one or a plurality of analytes and (f) a module for conserving the processed sample, in particular the conditioned sample, as well as (g) a module for sample conditioning that is different from (c), which is preferably a module for physical cell disruption or for removing the sample from closed primary sample vessels.

Here, the modules (c) and (d) are not in one unit. The unit has a first controller and communicates with a second unit over a data bus, whereas the modules within a unit each communicate over an additional data bus.

Each of this type of unit is advantageously situated in a separate, essentially closed housing. The housings can be detachably connected to one another, however. Similarly to one of the described units that is preferably enclosed, the combination of a plurality of units gives the impression to an observer that it is a single device.

Preferably, at least one unit of the device comprises one or a plurality of areas for storing used and/or unused consumables, wherein the storage area(s) for the unused consumables is (are) preferably spatially separated from the storage area(s) for the used consumables.

Preferably, the device includes a controller that comprises specific information of the processes and/or process parameters and which checks, depending on previously defined properties of the consumables and of the selected process determined prior to the process, whether the selected process is viable, and if necessary, signals discrepancies and/or offers possibilities to resolve the discrepancies.

It is further preferred that at least one of the units of the device includes a controller that comprises specific information on various types of consumables, preferably on their required quantities for a planned process sequence as well as on the shape, the dimensions, the capacity and the contents of sample vessels, process vessels (such as reaction vessels, wash vessels, elution vessels and/or mixing vessels) and/or storage vessels, and wherein this information, after the determination of one or a plurality of previously defined properties of the consumables prior to the start of the process sequence, preferably during the loading of the device, is utilised by means of sensor technology, preferably by a laser sensor and/or a digital camera and/or an ultra-sound sensor for the process sequence.

This allows the operator, before the start of the process, to check the complete loading of the device, which can show, for example, whether sufficient disposables and reagents are available for the selected process and/or whether the disposables are suitable for the procedure, for example in regard to their volume. The controller advantageously shows directly a possible or recommended action of the user, so as to correct the shown discrepanc(y)ies. When the user follows this action, he can carry out a new check and then if in agreement, can start the process.

During a process sequence for processing a sample in the unit that includes the module for sample conditioning, preferably at least two, preferably geometrically identical process vessels and preferably at least one additional sample vessel that is geometrically different from these are used, wherein the sample vessel is neither a process vessel nor a storage vessel.

Here, the sample or at least part of it is transferred into a process vessel, such as e.g. a reaction vessel, in which, for example the lysis is intended to occur as the conditioning process. Alternatively, already lysed samples can be submitted to the device, the lysed sample being also directly introduced into the extraction vessel. The elution of the separated carrier matrix with the bound analytes then preferably takes place in a new process vessel.

In order to avoid various vessels with different geometries having to be stored in the device, which to all intents and purposes is generally possible, it is particularly advantageous that the process vessels in the sample conditioning unit, particularly the vessels in which the lysis, the extraction and the elution take place, have the same geometric shape. Prior to the elution, one or a plurality of optional washing steps can take place, which likewise preferably each take place in a new vessel with the identical geometric shape.

By default, the eluates are transferred into a multi-well plate, for example a 96 well plate, for disbursement from the sample-conditioning unit. However, the transfer can be optionally made in another format that is particularly suitable for the desired sequential process.

A process vessel and one or a plurality of additional process vessels and/or storage vessels, which independently of each other can be geometrically identical or different with one another and with the first process vessel, are preferably used in the unit that includes the module for the preparation of a sequential reaction, particularly an amplification reaction and/or an analytical process.

Depending on the planned sequential process, the selected preparation process preferably takes place in the output process vessel of the previous unit. However, it is also possible to transfer the samples into other vessels. Particularly for the subsequent implementation of a PCR reaction or other processes, in which firstly the addition of additional reagents or mixtures is required, the necessary reagent mixture, e.g. PCR Mastermix, is advantageously already prepared as a finished mixture in a storage vessel, for example, or mixed in the apparatus itself. The reaction solution that has to be added can also be mixed in a storage vessel that delivers the reagent for the complete process. It would also be possible to prepare the required mixed reagent solution directly in the process vessels that could be both pre-filled and also filled in the apparatus. The eluate can then be added directly into the process vessels filled with reagents.

Preferably, at least one unit of the device possesses a transfer installation for transporting a sample vessel between two units, wherein this transfer module preferably includes a telescopic arm and/or a conveyor belt and preferably works bidirectionally. Depending on the technical design, the transfer module can effect the transfer into both the upstream unit and the downstream unit and also into only one of these units. In the last case, the upstream or downstream unit, into which the transfer is not possible from the neighbouring unit, must include its own transfer module. Preferably, at least the sample-conditioning unit includes a transfer module.

A further aspect of the invention relates to a module for use in the abovementioned unit for processing biological samples. It includes a rack for at least one vessel, a microcontroller and a data bus interface for data communication with the unit controller.

Preferably, at least one module of the device possesses a transfer installation for transporting a sample vessel between two units, wherein this transfer module preferably includes a telescopic arm and/or a conveyor belt and preferably works bidirectionally.

In addition, the module preferably includes a read-only memory and/or an internal memory and/or an electronic circuit for controlling communications. The module preferably possesses an interface to a CAN data bus. The microcontroller preferably works with a real-time operating system.

In an alternative embodiment, the module includes a microprocessor instead of the microcontroller.

As the above described modules are comprised in one or a plurality of the above described units and at least two of these units are again comprised in the device, the descriptions of each of the inventive subject matters (module, unit, device) are also valid for each of the other inventive subject matters, in so far as this is not explicitly excluded or makes no technical sense.

The details of the invention are discussed below with various examples with reference to the attached drawings.

In which are shown.

In the following description of various embodiments of the present invention, the functionally identical features of the different embodiments are given the same reference numeral.

Figure 1:
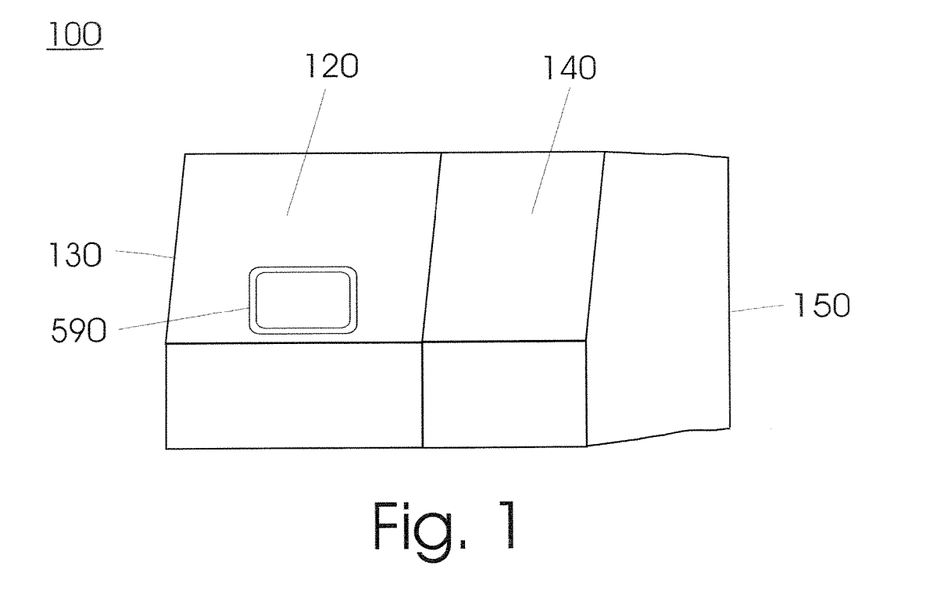
FIG. 1 a schematic illustration of a device according to one of the embodiments of the present invention.

FIG. 1 shows a typical embodiment of the invention. A device (100) serves to isolate and concentrate an analyte from a biological sample and to prepare a sequential process, such as for example an amplification reaction, analysis and/or a modification. It includes a plurality of units (120, 140) that are structurally separate from each other and are located in two housings (130, 150).

Figure 2:
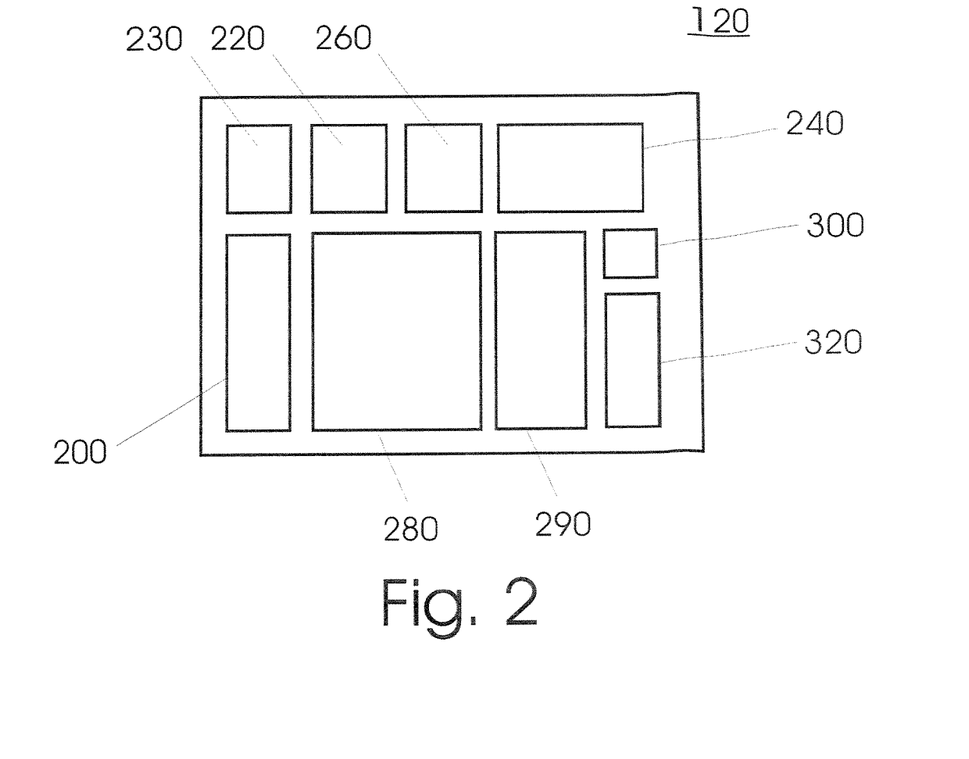
FIG. 2 a schematic illustration of a unit according to a further embodiment of the present invention.

FIG. 2 shows a schematic illustration of a number of modules that are consolidated in a first unit (120). This includes a module for receiving a sample vessel (200); a module (220) for lysing the sample material; an extraction module (240) that, after addition of a solid adsorption matrix in an upstream step, affords the separation of the desired sample constituents bound on the adsorption matrix from unbound sample constituents, the elution of the analytes from the adsorption matrix and the separation of the eluate from the adsorption matrix; a pipetting module (260) for aspirating and dispensing reagents, samples or process mixtures, such as the lysis mixture, the washing solution, the eluate, and for transferring samples; at least one area (290) for storing used, and, spatially separated there from, an area (280) for storing unused reagents or process mixtures, pipette tips, process vessels as well as sleeves, which can be present in suitable containers, wherein the storage areas can also be situated outside the housing, but are connected to it in some manner or other; a gripping module (230) for transporting sample vessels and/or process vessels within the unit as well as sleeve arrangements within the device (100); and a transfer module (300) for transferring one of the sample vessels containing the analytes to a second unit (140) of the device (100) or an apparatus from another manufacturer and optionally back again.

The operator passes one or a plurality of samples in one or a plurality of sample vessels through an entrance flap or drawer of the first unit (120) of the device (100) into the module for taking samples (200). There is typically a plurality of biological samples arranged in a plurality of wells of a sample plate; of course, according to the invention, provision is made for other sample vessels and sample holders known from the prior art such as, for example quite generally test tubes of various sizes, multi-well sample plates (e.g. 96, 48, 16, 12 or 8 well plates), PCR tubes or blood sample tubes optionally with appropriate holders. Alternatively, the sample material can also be transferred into the sample-receiving module (200) by a transfer module (300) of an upstream additional unit (110) that is equipped, for example, with a module (205) for the disruption of cell material. The operator inputs a required process on a touch screen of the user interface (590). The advancement of the process and possible checks and error messages can be observed on the monitor.

According to an embodiment of the invention, the device includes at least one controller (500) that possesses specific information on various types of consumables, preferably concerning their required amount for a planned process cycle as well as the shape, the dimensions, the holding capability and the capacity of sample vessels, process vessels and/or storage vessels. Before starting a process cycle, preferably during or after an operator has loaded the device (100), the controller, by means of a sensor technology, ascertains information on one or a plurality of previously defined properties of the consumables. The sensors are preferably of the laser sensor and/or digital camera and/or ultra-sound sensor design. The information acquired by the controller is utilised for the further process cycle.

After the cycle has started, a number of samples is partially or completely transferred by the pipetting module (260) into a process vessel that has wells for samples. For example, 50 µl to 10 ml, preferably 0.1 to 5 ml, particularly preferably 0.5 to 3 ml are transferred from the samples into a reaction vessel, in a quite particularly preferred embodiment 1 ml. Earlier, the reaction vessel was lifted up by the gripper of the gripping module (230) from a storage vessel in the storage area (280) of the unit (120). The reaction vessel is transported from the gripping module (230) into the area of the lysis module (220) and set down there. The reagents required for the lysis are then withdrawn by means of the pipetting module (260) from one or a plurality of storage vessels in the storage area (280).

After having removed the packaging, the operator can directly deposit any consumables required for the processes in the storage area (280) of the device (100). Additional sample carriers can be placed in the device (100) during an ongoing treatment process without influencing the ongoing process.

The reagent added first serves, for example, for the cell disruption in the sample in order to make available constituents of DNA, RNA, proteins or further cell constituents for additional process steps. Particles are then added which possess a surface with an adsorbing substance, preferably in the form of a suspension containing magnetic or magnetisable microparticles or micropearls, which are provided with an adsorbing substance on their surface.

Figure 12A:
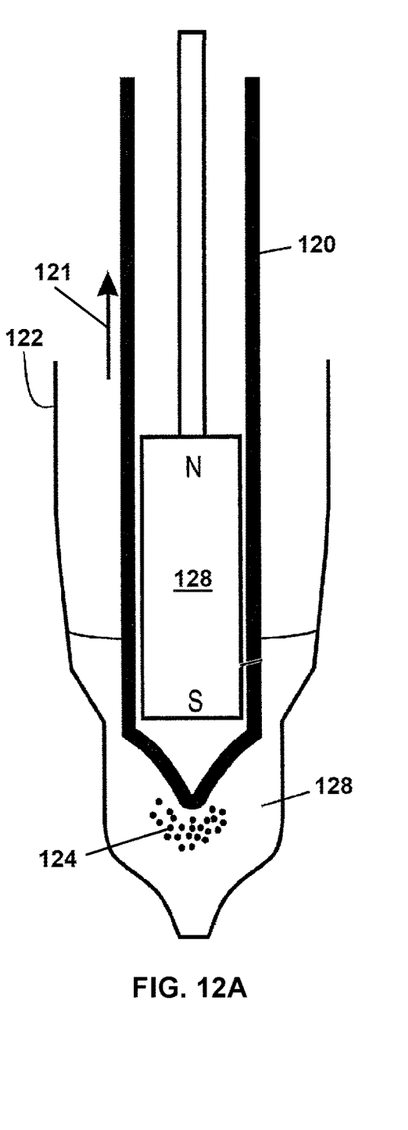
FIG. 12 a schematic illustration of first and second embodiments of plastic sleeves according to the present invention.

The analyte present in the solution after lysis, e.g. DNA, RNA and/or protein, now binds onto the surface with the adsorbing substance and thereby onto the particles. A magnetic separation then takes place in the extraction module (240). In the process the solution containing the microparticles is freed of the remaining constituents of the original sample, followed by one or a plurality of washing steps in order to obtain particles on which the purified analyte is bound. For this purpose, FIG. 12A shows an arrangement of plastic sleeves (120) is introduced from above into the reaction vessel (122) containing the microparticles (124) and the solution (126) to be purified, wherein the sleeves (120) possess a smaller diameter than the minimum diameter of the openings of the reaction vessels (122). The sleeves (120) are hollow inside, thin walled and open at their top ends lying furthest from the reaction vessels (122). Typically, they are arranged in a matrix design on a common carrier plate. Various embodiments are possible, for example with 8, 16, 24 and 48 sleeves. Preferably, a plurality, preferably three, two times four designs are used at the same time. The sleeve assemblies are recognised inside the unit (120) by sensor technology known from the prior art and managed by a controller (500).

Figure 12B:
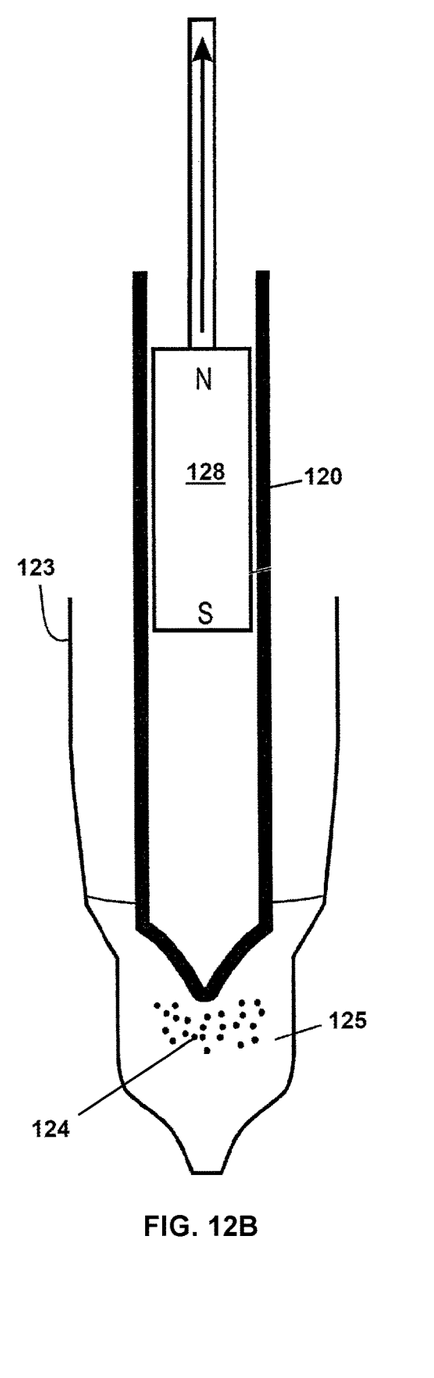

The lower end position of the sleeves (120) dips into the reaction vessels (122). A thin bar (128), which is preferably in the form of a continuous bar magnet, is now introduced from above into preferably each sleeve (120) of the assembly by means of the extraction module (240). Typically, this is a permanent magnet. In a lower cost variant, only the lower end of the bar that dips into the liquid is in the form of a magnet. Part of the magnet now finds itself under the level of the sample solution (126) in the process vessel (122), with the result that the magnetic particles (124) are attracted onto the outside of the plastic sleeve (120) and stick to it. A device, which is also used later on for oscillation generation, then synchronously removes the sleeves (120) with the bar magnets (128) located inside in a vertical direction upwards (121), whereby the particles (124) containing the adsorbed analytes are also removed from the solution. FIG. 12B shows the bars are then dipped into a second process vessel (wash vessel) (123). This was transported by a conveyor belt to the location of the first reaction vessel and is filled with a reagent (125) that is suitable for rinsing the adsorption matrix in order to remove the unwanted constituents of the solution. In order to effect as thorough as possible rinsing of the particle (124) with the reagent (125), the magnetic bars (128) are then removed though the upper part of the sleeves (120). The particles (124) sticking to the sleeves (120) are then no longer attracted by the magnet (128), therefore loosen themselves from the outside of the sleeves (120) and are collected through gravity in the wash vessel (123) located below the sleeve (120). In alternative embodiments of the invention, other process for magnetic separation are also possible, which are known from the prior art, for example the use of magnetisable particles instead of magnetic particles and electromagnets that can be switched off instead of permanent magnets, as well as other extraction processes.

Preferably, the abovementioned device for oscillation generation is used in the extraction module (240) to set the sleeves vibrating when dipped in the solution. This vibration is transferred to the sample liquid containing the particles and causes the particles to be resuspended in the wash solution or eluant. After a defined time the magnetic bars are re-engaged into the sleeves. The particles are once more magnetically attracted onto the outside of the sleeves and withdrawn with them upwards out of the reaction vessels. Then, as in the first passage, a further reaction vessel is brought in filled with fresh reagent. These rinsing steps of the particles are repeated several times, depending on the preset parameters of the specific process. Alternatively, it is possible not to carry out the several wash or rinse steps, rather directly after the previous step of disruption of the sample material to proceed with a further step, preferably the elution described below.

In order to separate the adsorbed analytes from the particles, in a further step the sleeves with the adhering particles are introduced into a further process vessel. This is filled with a reagent that is suitable for separating the analyte from the particles (elution). After detaching the particles from the bars and a vibratory mixing as in the previous steps, there remains after this step a solution of the analyte in the elution reagent. The particles are now bound onto the sleeve a last time by introducing the magnetic bar and removed from the solution in the upward direction. They are disposed of in a container in the disposal area (290) of the unit (120). Beforehand, the eluate present was withdrawn out of the process vessel by the pipetting module and transferred into a process vessel with the desired output format, which is located in a starting storage area (320) of the unit (120). From there the output process vessel containing the extracted sample can be taken out by an operator for further treatment, or, preferably, sent to a second inventive unit (140) for further processing. A transfer module (300) is provided for this purpose, which relays the output process vessel by means of a transport device known from the prior art, preferably a bidirectional telescopic arm or a bidirectional transport belt, through an opening preferably in the side wall of the housing (130) to a sample reception module (200) of the second unit (140).

Figure 3:
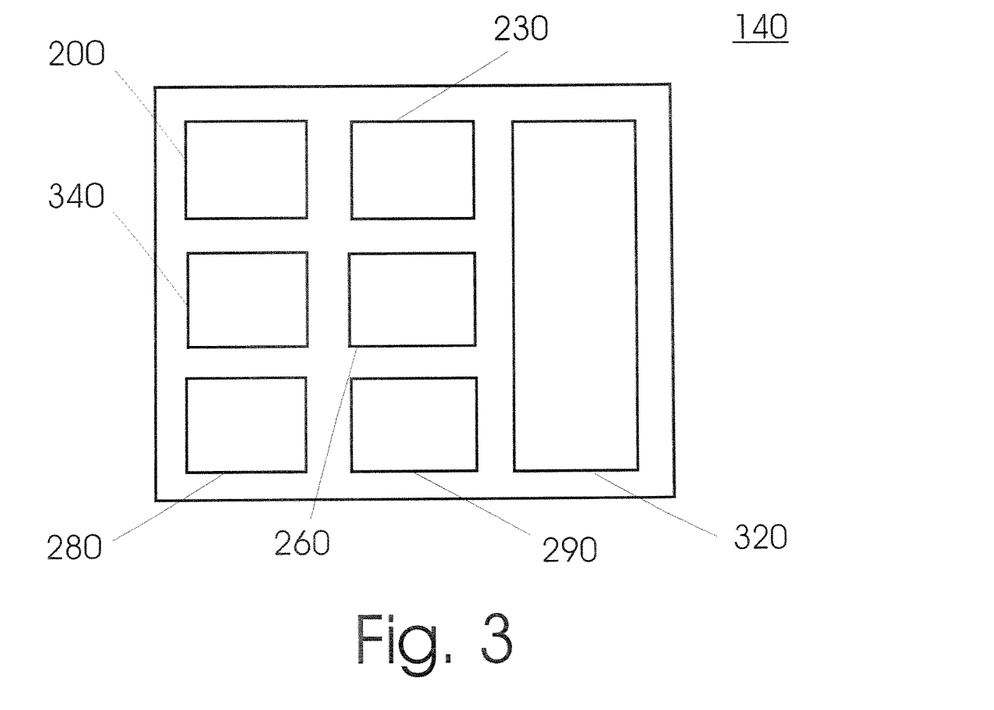
FIG. 3 a schematic illustration of a further unit according to a further embodiment of the present invention.

FIG. 3 shows a schematic illustration of a second unit (140) inside the device (100) according to a further embodiment of the present invention. The unit includes a module for the reception of process vessels (200), an optionally cooled storage area (340) for reagents, a storage area (280) for storing consumables such as pipette tips or process vessels, which are preferably found in appropriate multi-pack containers, as well as a disposal area (290) for used consumables.

A pipetting module (260) serves for adding reagents to the sample solution containing the isolated analyte. In this way the analyte is prepared, for example, for carrying out an amplification reaction such as a polymerase chain reaction (PCR) or for an assay for the analysis of a protein. It is also possible to carry out a course of different sequential processes with different samples if this does not require different technical conditions. The information, on which reagents are to be used for a specific sample, is received by the second unit (140) over the data bus connection (400) from the control module of the first unit (120). A starting storage area (320) serves as the intermediate storage for the output process vessel containing the analytes. The sample vessel can be removed from this area by an operator for further treatment. In a typical embodiment, an optional transfer module (300) serves to send the sample vessel to an additional unit (160), in which a sequential reaction, typically an amplification reaction such as a PCR or an analysis is carried out. In order to prevent cross contamination, the pipettes used to add reagents to the samples are disposed of after a single use in one or a plurality of waste containers inside the storage area (290) of the unit (140). It would also be possible to provide the storage area or at least a part of it outside the unit or the device, wherein the storage area should be detachably connected to the unit or the device.

Figure 4:
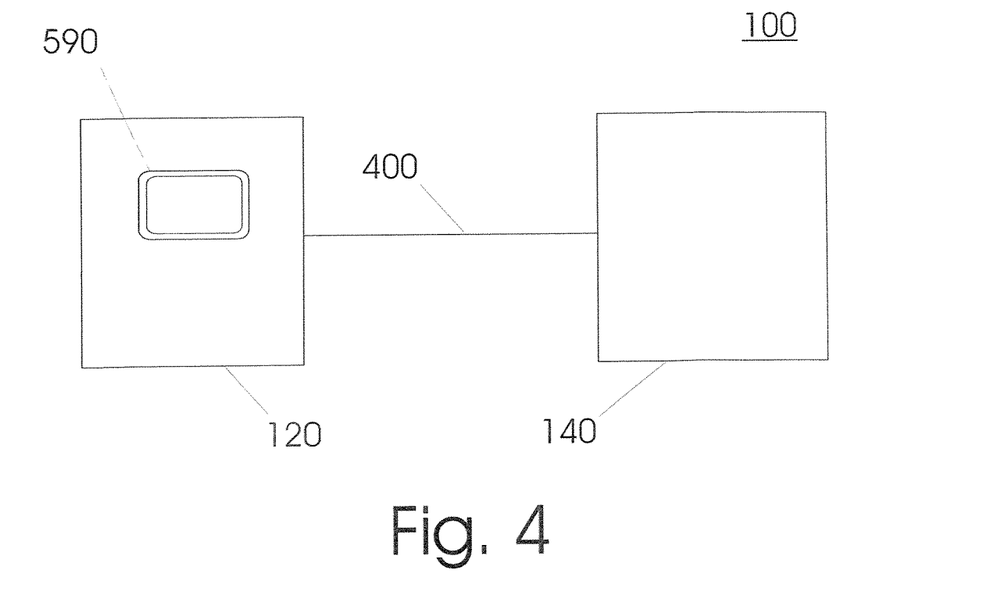
FIG. 4 a schematic illustration of a device according to a further embodiment of the present invention.

FIG. 4 shows a further embodiment of the invention, according to which units (110, 120, 140, 160, 180) of the device (100) are linked over a first data bus (400). This is schematically illustrated in FIG. 4 for a device with two units (120, 140). Various topologies are possible, preferably a star emanating from a unit, a ring or the connection over a common switch. In an embodiment of the invention, this data bus is realised according to the Ethernet standard.

According to a further embodiment, the conditioned sample from the second unit (140) is delivered by a transfer module (300) to an additional unit (160). This includes a PCR module (170), optionally also a detection module (360) for detecting the analyte. The detection module can also be pre-positioned in a further unit (180).

Figure 5:
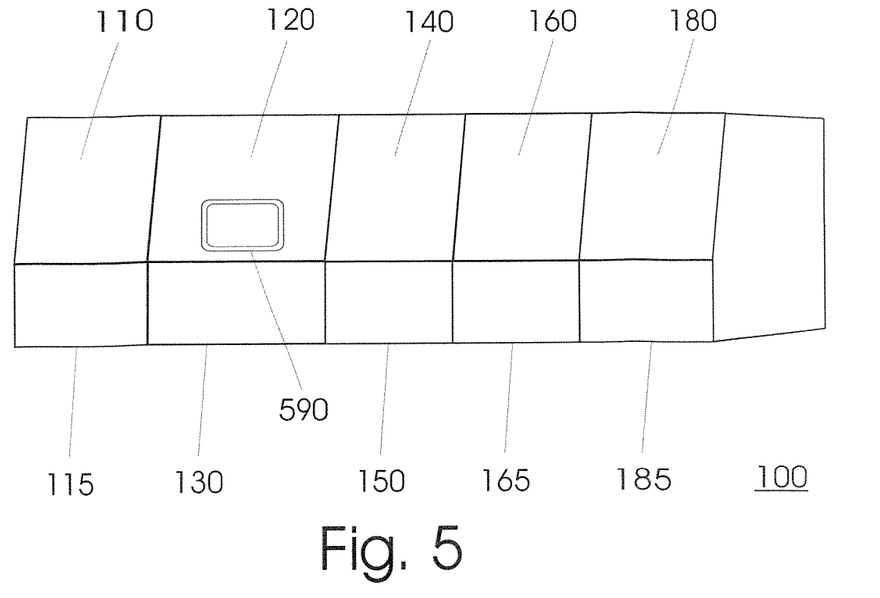
FIG. 5 a schematic illustration of a device according to a further embodiment of the present invention.

FIG. 5 shows an embodiment of the invention, in which the device (100) is constructed out of five units (110, 120, 140, 160, 180) that each has its own housing (115, 130, 150, 165, 185), intended to be detachably connected with each other, however. Outwardly, it preferably gives rise to the impression that it is a single apparatus.

Figure 6:
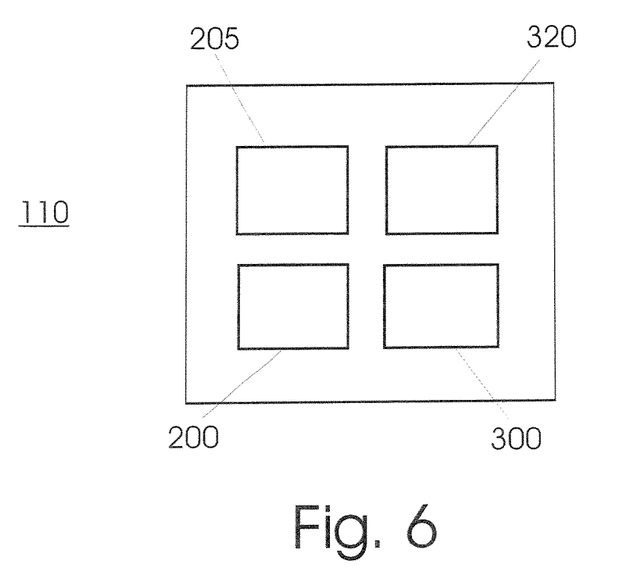
FIG. 6 a schematic illustration of a unit for cell disruption according to a further embodiment of the present invention.

FIG. 6 shows the schematic layout of a unit (110) for the physical cell disruption according to an embodiment of the invention. The unit includes at least one module for receiving samples (200), a module for cell disruption (205), a transfer module (300) that is only optional however, as well as an output storage area (320).

Figure 7:
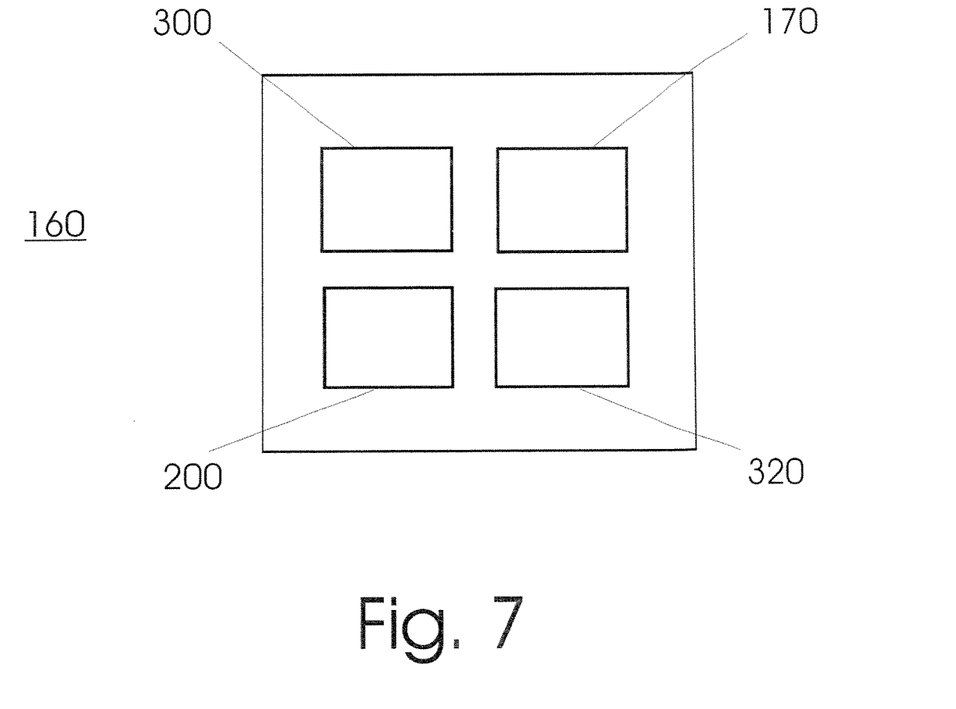
FIG. 7 a schematic illustration of a unit for the amplification of an analyte according to a further embodiment of the present invention.

FIG. 7 shows the schematic layout of a unit (160) for implementing a polymer chain reaction according to an embodiment of the invention. The unit includes at least one module for receiving samples (200), a PCR module (170), a transfer module (300) as well as an output storage area (320).

Figure 8:
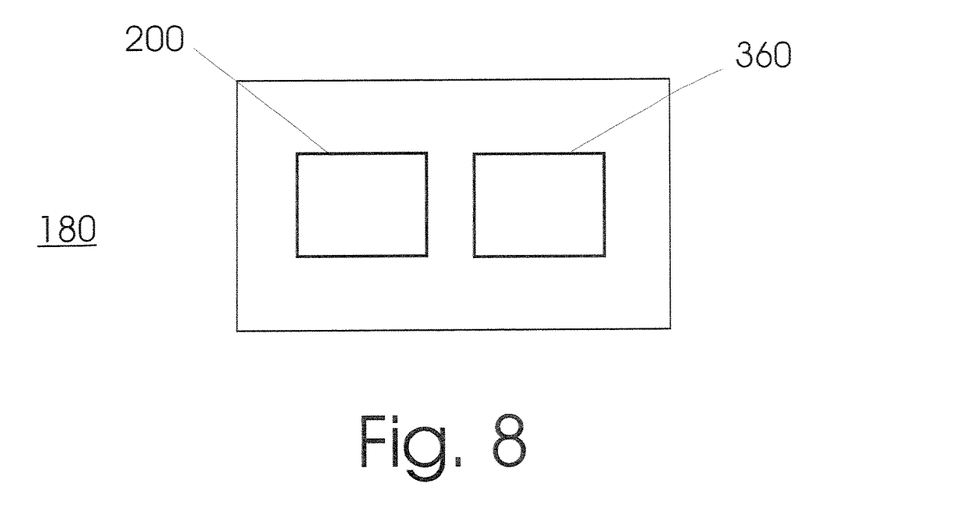
FIG. 8 a schematic illustration of a detection unit according to a further embodiment of the present invention.

FIG. 8 shows the schematic layout of a unit (180) for detecting one or a plurality of analytes according to an embodiment of the invention. The unit includes at least one module for receiving samples (200) as well as a detection module (360).

Figure 9:
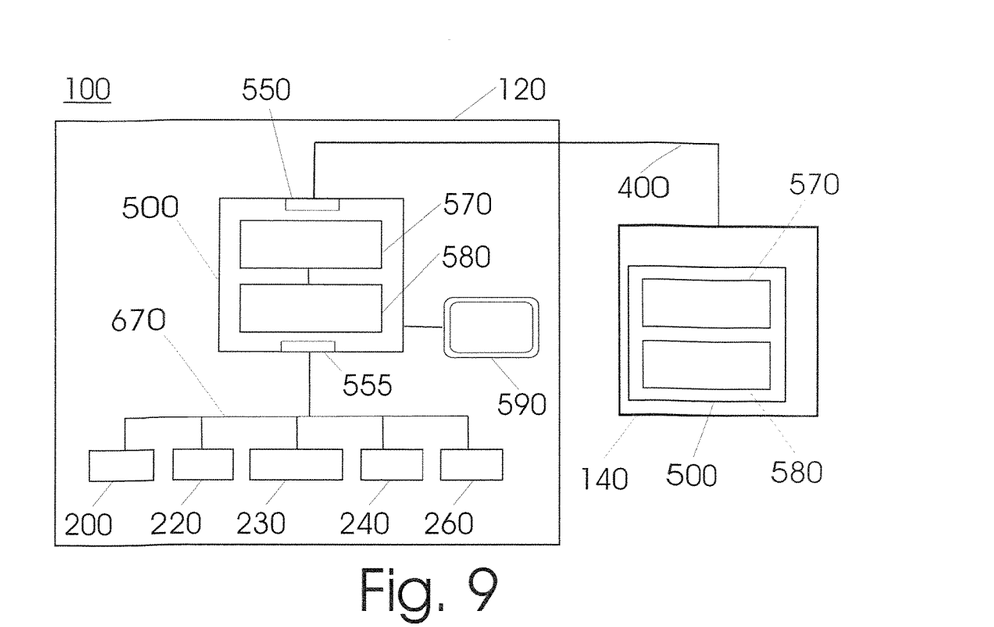
FIG. 9 a schematic illustration of a block diagram of a device according to a further embodiment of the present invention.

FIG. 9 shows a schematic illustration of a device (100) according to an embodiment of the invention, wherein the layout of the first unit (120) with its modules is shown connected to a schematically illustrated second unit (140). The control module (500) is the central entity for controlling the events in a unit (110, 120, 140, 160, 180). It possesses an operating system (570) and at least one software application (580) that serves to control and regulate the functions of the single modules and their cooperation. The control module can communicate over the external interface (550) over a first data bus with the control module of a second unit (140). The control module (500) is connected over a second interface (555) with further modules (200, 220, 230, 240, 260) over a second data bus (670) inside the unit (120).

Figure 10:
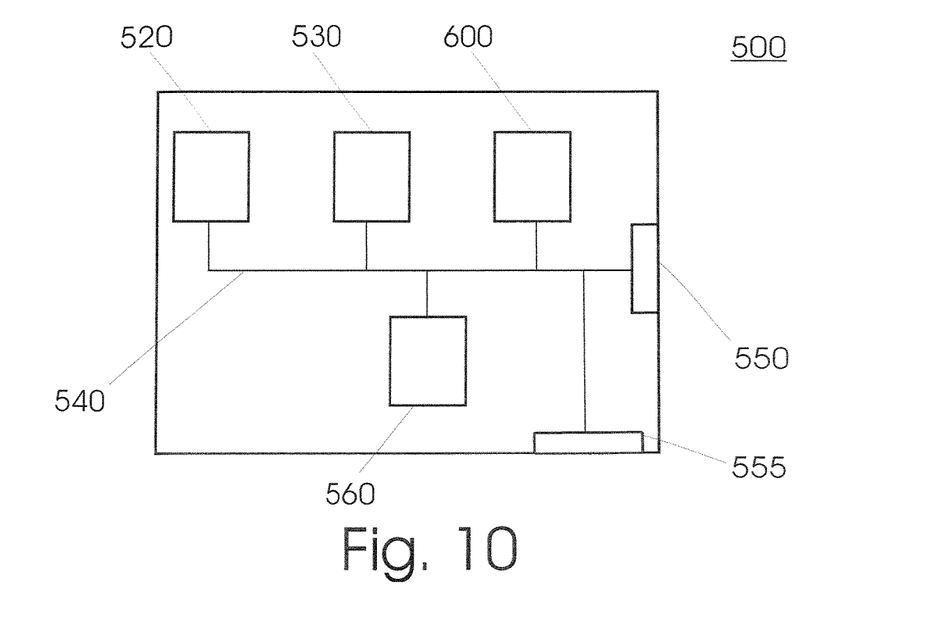
FIG. 10 a schematic illustration of a block diagram of a control module according to a further embodiment of the present invention.

FIG. 10 shows the block diagram of a control module (500) of a unit according to an embodiment of the invention. The control module (500) is typically realised in the form of a computer with a microprocessor (520), an internal memory (530), an internal bus (540), an external interface (550) to a first data bus (400), and a control chip assembly (560). The control module (500) is connected over a second interface (555) with further modules over a second data bus (670) inside the unit.

If more than one unit (110, 120, 140, 160, 180) of the device (100) possess a control module (500), one of the units assumes a dominant role in a master/slave operation. The input of orders by an operator to the device is made over an operating surface (590) that is typically provided in the form of a touch screen on a front side of the housing (130) of the first unit (120). The control commands includes for example the initialisation of the device (100), the start of a work cycle and the input concerning which analyte and optionally with which process the sample should be examined.

All process steps are automatically checked and verified by the control module (500). Particularly after the set up of consumables, a check is made on whether they were correctly set up, if other specific information on various types of consumables that were previously defined, such as preferably their required amount for a planned process cycle as well as the shape, the dimensions, the holding capability and the capacity of sample vessels, process vessels and/or storage vessels is established, which serves to check the process requirements and should show discrepancies from the selected protocol. In the same way, after the automatic or manual entry of a sample vessel into the entrance area, the parameters of the sample vessel are determined by means of sensors.

The control module sends control signals to the individual function modules and receives information on the status and parameters from the modules. In special cases, the control module (500) also initiates direct communication between individual modules, for example for events such as the unauthorised opening of the housing (130, 150) by a person, which requires a rapid reaction. The data bus (670) is typically a standard data bus used in automation technology; in a preferred embodiment of the invention it is a CAN (controller area network). The modules possess a standard interface (680) to the data bus (670).

In an embodiment, the controller possesses a memory card (600) as the memory module for the operating system (570), the applications (580) and equipment specific data such as information on various types of consumables. In a further embodiment, the control module is additionally equipped with a hard disk.

According to a further embodiment of the invention, the control module also possesses a module for remote maintenance, which provides status information over the Internet. In this way in the case of errors or maintenance, remote maintenance and remote diagnoses are made possible. In this case a technician can already take the matching replacement module to the site of the device, thereby also reducing service costs and down time.

According to the invention, all modules are structurally separate from each other and in essence can be removed from a unit (110, 120, 140, 160, 180) without disassembling another module. This modular construction offers many advantages. In the case of a system malfunction, a service engineer can quickly identify the defective module. By the exchange with a refurbished or new replacement module, the source of failure can be eliminated with minimal effort and down time.

A significant advantage of the modular construction is the possibility of equipping the device with additional or other modules. An example is a starting module that in addition enables the automatic recognition of the shape of the incoming sample vessel, preferably a multi-well sample plate, by bar code scanning or size recognition by means of laser scanning. At the same time, the apparatus can subsequently be quickly and cheaply equipped with previously uninstalled, functional modules in one or a plurality of existing units or in the form of a complete, new unit. Thus, the optional additional unit (160), in which e.g. a PCR will be carried out, can be subsequently equipped with a detection module (360) in order that the process chain from the sample input to the output of the analytical result can be fully displayed in the device (100).

Figure 11:
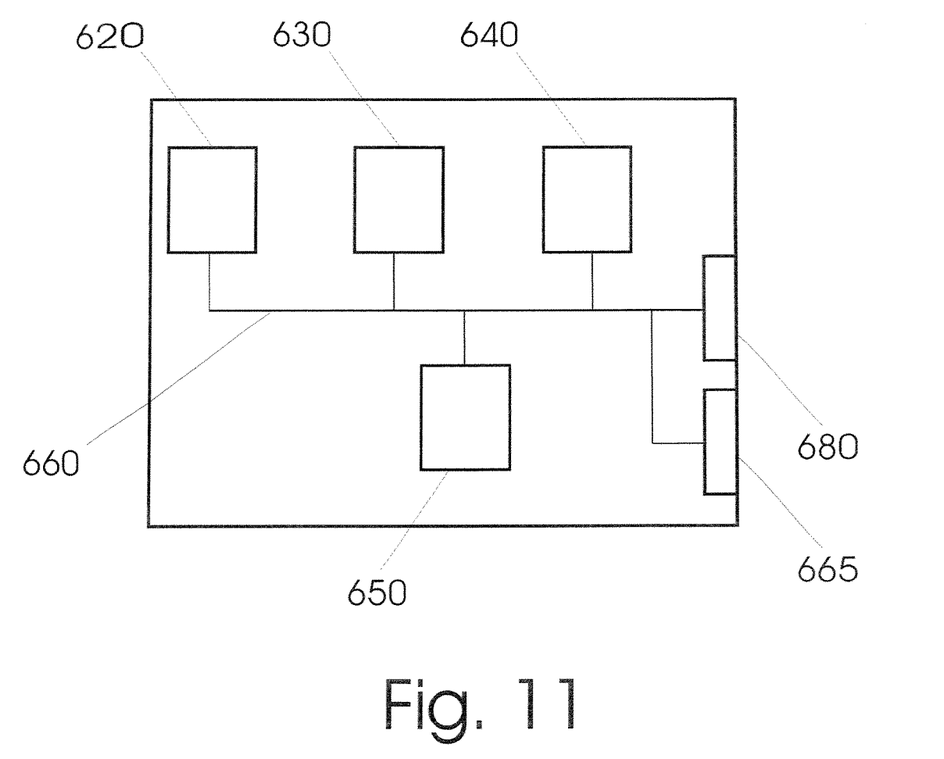
FIG. 11 a schematic illustration of a block diagram of a block diagram of the microcontroller control of a module according to a further embodiment of the present invention.

According to a further embodiment of the invention, each of the individual modules possesses a microcontroller (620) that controls the progress inside the module and the communication with the central control module (500) and/or other modules. FIG. 11 shows a block diagram of a microcontroller according to an embodiment of the invention. The microcontroller can be realised as a single chip device or combined with additional components such as internal memory (630), read only memory (640) and input/output chips (650), with which it communicates over an internal bus (660). The microcontroller communicates with additional components of the module, such as for example sensors and actuators, over an input/output interface (665). In a typical embodiment of the invention, the microcontroller works with a real-time operating system (660). According to an alternative embodiment, the module possesses a microprocessor instead of the microcontroller (620).

According to a further embodiment of the invention, a module, typically the control module (500), possesses information concerning the shape, the dimensions and the holding capacities of a plurality of different sample vessels, for example in the form of a data bank. A number of commercially available sample vessels and sample plates are preinstalled in it. The type of sample vessel is recognised by the acquisition of the dimensions by means of a bar code scanner or a laser scanner. The parameters relating to the shape, the holding capacity of the individual wells and the dimensions of the carrier plate are taken into account by the control module for further treatment according to the employed carrier plate. In this way, the operator can work with different carrier plates without manual intervention. Each type of sample vessel solely requires the use of an appropriate adapter that is supplied by the operator.

In a further embodiment of the invention, after entering the device the samples from the sample carrier are successively transferred by means of the pipetting module (260) into one or a plurality of process vessels that are used in the further process steps inside the unit (120, 140).

In an embodiment of the invention, a container is provided in the storage area (280) for unused sleeve arrangements and the process vessels, which enables an orderly and space-saving storage. The consumables are introduced in containers by an operator through a drawer into the unit (120). Rails inside the container serve as a guide for the unloading carried out by the gripping module (230). Once emptied during usage, the now empty container is preferably used for the storage of used sleeve arrangements and of process vessels or other disposables.

The sleeve arrangements and the process vessels are stackable for space-saving storage. Pipette tips are supplied through the same drawer. The storage area for additional waste materials is accessible through a drawer.

The described device (100) with units and modules possesses a series of advantages. Automated devices for sample preparation are constructed from a great number of components and by the interplay of the assemblies exhibit a high degree of complexity that contributes to maintenance costs and susceptibility to error.

Against a background of increasing cost pressures and the resulting increased rationalisation in the health care sector, the requirements for cost effectiveness for this type of laboratory equipment are also increasing, however. The high level of ease of maintenance, the simple diagnostic possibilities over the internet and the fastest possible exchangeability of modules resulting from the modular design provided by the present invention contribute to a reduction in running costs. Consequently, the sum of the costs associated with the lifetime of the equipment, also called "Total Cost of Ownership" (TCO) is reduced. Above all, maintenance costs and down times can be minimised by the described construction, all of which was only barely considered in this form in the prior art up to now.

Moreover, a very user-friendly, customisable device that can be self-assembled and combined as needed, is made available to the user. Based on the possibility of continuous process control from the primary or secondary sample to the required result (Tube to Result), without the user's presence being required after the start up to the receipt of the result, this additionally offers a significant alleviation of work and enables an efficient utilisation of time of the user.

The invention is also directed to an apparatus for carrying out the disclosed methods and including apparatus parts for performing each described method steps. These method steps may be performed by way of hardware components, a computer programmed by appropriate software, by any combination of the two or in any other manner. Furthermore, the invention is also directed to methods by which the described apparatus operates. It includes method steps for carrying out every function of the apparatus.

The invention claimed is:

1. A device configured to process samples, comprising:
a module configured to receive and/or output at least one of a sample vessel and a process vessel,
a transport module configured to transport the process vessel,
a sample conditioning module configured to perform sample conditioning, and
comprising a lysis module and an extraction module,
wherein the extraction module comprises at least one plastic sleeve comprising a hollow region inside the sleeve and at least one magnet removably disposed inside the hollow region,
wherein, when the at least one magnet disposed inside the hollow region is positioned inside the process vessel, the at least one magnet attracts at least one analyte bound to a magnetic particle onto the outside surface of the sleeve,
a preparation module configured to prepare a sequential process for the at least one analyte,
a plurality of control modules configured to recognize the type of a sample vessel, by acquisition of the dimensions by means of at least one of a bar code scanner and a laser scanner,
wherein the modules are dispersed throughout a plurality of units connected by a first data bus, wherein a first unit comprises the sample conditioning module, a second unit comprises the preparation module, each of the first and second units comprises a control module, and one of the units comprises a plurality of modules connected by a second data bus,
wherein each unit is placed in a separate housing, such that the sample conditioning module is structurally separate from the preparation module, and wherein the housings are removably connected such that each housing can be removed without removing another housing, and wherein each of the modules comprises a microcontroller or microprocessor configured to control progress inside the module and communication with another module.

2. A device according to one of claim 1, further comprising:

an additional sample conditioning module connected upstream of the sample conditioning module, wherein said additional sample conditioning module comprises neither a lysis module nor an extraction module, but rather a module configured to at least one of disrupt physical cells and remove the sample from closed primary sample vessels.

3. A device according to claim 1, further comprising:

a transfer module configured to transport a process vessel between two units, wherein the transfer module includes at least one of a telescopic arm and a conveyor belt and is configured to work bi-directionally.

4. A device according to claim 1, further comprising:

a controller that comprises specific information of a processes and/or a process parameter and is configured to check whether a selected process is viable, and if necessary, signals a discrepancy and/or offers a possibility to resolve the discrepancy.

5. A device according to claim 1, wherein a unit is configured to deliver an output process vessel in various starting formats.

6. A device according to claim 1, wherein a unit is configured to be connected with an external computer, by which a parameter of the device can be adjusted and/or called.

7. A device according to claim 1, wherein a unit comprises a storage area for storing used consumables and a storage area for storing unused consumables, wherein the storage area for unused consumables is spatially separated from the storage area for used consumables.

8. A device according to claim 1, further comprising:

a controller configured to possess specific information on various types of consumables, wherein after a determination of a previously defined property, said specific information is utilized by a sensor technology.

9. A device according to claim 1, further comprising:

a module configured to receive sample vessels, which is configured to be converted by an adapter to accept a plurality of different sample vessels.

10. A device according to claim 1, wherein during a process cycle of processing a sample:

a plurality of process vessels and a sample vessel are used, in a unit that comprises the module for the sample conditioning, a first process vessel, and a second process vessel and/or a storage vessel which are geometrically identical or different from one another and from the first process vessel, are used in a unit that comprises the module for the preparation of a sequential process, wherein the sample vessel is neither a process vessel nor a storage vessel.

11. A device according to claim 1, comprising a module for use in a unit for processing biological samples, the module comprising:

a holder configured to hold a vessel, the microcontroller or microprocessor, a data bus interface configured to communicate data with the controller of the unit.

12. A module according to claim 11, with a transfer mechanism for transporting a sample vessel and/or process vessel between two units, wherein the transfer module possesses a telescopic arm and/or a conveyor belt and works bi-directionally.

13. A module according to claim 11, wherein the microcontroller is configured to work with a real time operating system.

14. A module according to claim 11, further comprising at least one of:

a read-only memory, an internal memory, and an electronic circuit configured to control communications.

15. The device of claim 1, wherein at least one of the control modules is configured to store the information concerning, dimensions, and holding capacities of a plurality of different sample vessels, in a data bank comprising a number of preinstalled sample vessels comprising tubes and multi-well sample plates.

16. The device of claim 1, wherein the units are configured to appear to be a single device.

17. The device of claim 1, wherein the second data bus comprises a Controller Area Network (CAN) bus.

18. The device of claim 1, wherein the plurality of modules connected over a second data bus each have a single interface to the second data bus.

19. The device of claim 1, further comprising:

a sequential processing module, configured to implement a sequential process.

20. The device of claim 1, further comprising:

an analysis module, configured to implement an analysis of an analyte.

21. The device of claim 2, wherein the additional sample conditioning module is provided in an additional unit.

* * * * *